United States Patent [19]

Dorme et al.

[11] Patent Number: 5,237,066
[45] Date of Patent: Aug. 17, 1993

[54] ENANTIOMERS OF ABSOLUTE CONFIGURATION S OF AMIDE DERIVATIVES OF 3-AMINOQUINUCLIDINE, THE PROCESS FOR PREPARING THEM AND THEIR APPLICATION IN THERAPY

[75] Inventors: Nicole A. M. Dorme, Paris; Alain J. L. Renaud, Rueil Malmaison; Michel Langlois, Buc, all of France

[73] Assignee: Delande S.A., Courbevoie, France

[21] Appl. No.: 760,921

[22] Filed: Sep. 17, 1991

Related U.S. Application Data

[62] Division of Ser. No. 149,358, Jan. 28, 1988, abandoned.

[30] Foreign Application Priority Data

Feb. 4, 1987 [FR]  France ............................... 87 01355

[51] Int. Cl.$^5$ ............................................. C07D 453/02
[52] U.S. Cl. .................................................... 546/133
[58] Field of Search ........................................ 546/133

[56] References Cited

U.S. PATENT DOCUMENTS 4,593,034  6/1986  Munson, Jr. et al. ............... 514/305
4,657,911  4/1987  Imbert et al. ....................... 514/272

*Primary Examiner*—Marianne M. Cintins
*Assistant Examiner*—Catherine Scalzo
*Attorney, Agent, or Firm*—Roylance, Abrams, Berdo & Goodman

[57] ABSTRACT

Enantiomer of absolute configuration S of formula:

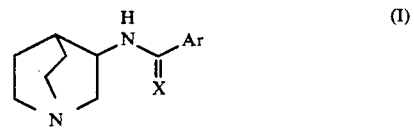

where:
X=O or S; and
Ar denotes a:
* phenyl ring substituted with one, two or three $C_1$-$C_4$ alkoxy groups;
* phenyl ring substituted at the 2-position with a $OCH_3$ group and at the 5-position with a halogen atom or a lower alkylcarbonyl group;
* phenyl ring substituted at the 2-position with $OCH_3$, at the 4-position with $NH_2$ or alkylcarbonyl-NH and at the 5-position with a halogen;
* 3-fluoro-2-methoxyphenyl group;
* 5-pyrimidinyl group substituted at the 2-position with $NH_2$ and in the 4-position with alkoxy or phenyloxy.

These compounds are useful as medicinal products having activity in respect of gastric movements and antiemetic activity.

2 Claims, No Drawings

ENANTIOMERS OF ABSOLUTE CONFIGURATION S OF AMIDE DERIVATIVES OF 3-AMINOQUINUCLIDINE, THE PROCESS FOR PREPARING THEM AND THEIR APPLICATION IN THERAPY

This is a division of application Ser. No. 07/149,358 filed Jan. 28, 1988 now abandoned.

The subject of the present invention is the enantiomers of absolute configuration S of amide derivatives of 3-aminoquinuclidine, the process for preparing them and their application in therapy.

Amide derivatives of 3-aminoquinuclidine, corresponding to the formula:

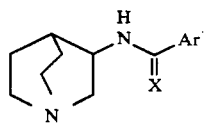

in which:

X denotes an oxygen or sulphur atom; and
Ar has one of the following meanings:
*) a phenyl ring substituted with one, two or three $C_1$–$C_4$ alkoxy groups; .
*) a phenyl ring of structure:

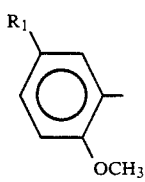

Where $R_1$ denotes a halogen atom or an alkylcarbonyl group in which the alkyl group contains from 1 to 4 carbon atoms;
*) a phenyl group of structure:

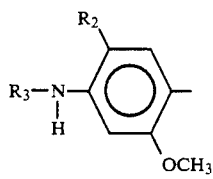

where $R_2$ denotes a halogen atom and $R_3$ is a hydrogen atom or an alkylcarbonyl group in which the alkyl residue contains 1 to 4 carbon atoms;
*) a 3-fluoro-2-methoxyphenyl group; or
*) a 5-pyrimidinyl group of structure:

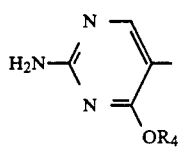

where $R_4$ denotes a $C_1$–$C_4$ alkyl group or a phenyl ring,
the addition salts of these derivatives with an organic or inorganic acid, as well as the hydrates of these derivatives and salts, are already known from EP-A-0,099,789.

The above derivatives of formula (I), salts and hydrates have, however, been described, in EP-A-0,099,789, only in the form of their racemic mixture. In the course of studying the racemic mixture of these compounds, the applicant endeavoured to synthesize the two enantiomers corresponding to each racemic mixture. After overcoming the problem presented by this synthesis, he studied the pharmacological properties of these enantiomers and was thus able to observe that, altogether unexpectedly, the enantiomers of absolute configuration S had a pharmacological behaviour that was very different both from that of the corresponding racemic mixtures and from that of their antipodes of absolute configuration R.

Consequently, the subject of the present invention is the enantiomers of absolute configuration S of the above derivatives of formula (I), salts and hydrates. Its subject is, in addition, the processes for preparing these enantiomers, as well as the application of these enantiomers in therapy.

The enantiomers according to the invention may be obtained by the resolution of racemic mixtures or by stereospecific synthesis.

The stereospecific synthesis consists in: (i) either condensing laevorotatory 3-aminoquinuclidine of configuration S with, respectively, acids or thioacids of formula:

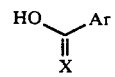

where X and Ar have the same meaning as in formula (I), in particular in the presence of dicyclohexylcarbodiimide, (ii) or condensing laevorotatory 3-aminoquinuclidine of configuration S with the chloride of, respectively, acids or thioacids of formula:

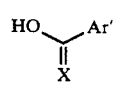

where X has the same meaning as in the formula (I) and Ar' assumes one of the following meanings:
*) a phenyl ring substituted with one, two or three $C_1$–$C_4$ alkoxy groups;
*) a phenyl ring of structure:

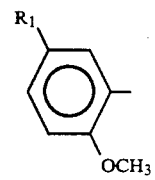

where $R_1$ denotes a halogen atom or an alkylcarbonyl group in which the alkyl group contains from 1 to 4 carbon atoms;
*) a phenyl group of structure:

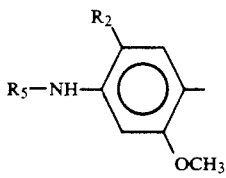

where $R_2$ denotes a halogen atom and $R_5$ is an alkylcarbonyl group in which the alkyl residue contains 1 to 4 carbon atoms;
*) a 3-fluoro-2-methoxyphenyl group; or
*) a 5-pyrimidinyl group of structure:

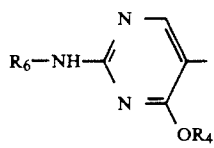

where $R_4$ denotes a $C_1$-$C_4$ alkyl group or a phenyl ring and $R_6$ denotes an acetamido group,
which leads to the enantiomers of absolute configuration S of formula:

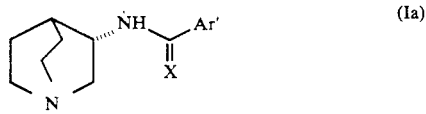

(Ia)

where X and Ar' have the same meaning as in the formula (III), and then, if required, subjecting the enantiomers of the formula (Ia) and having the particular structures:

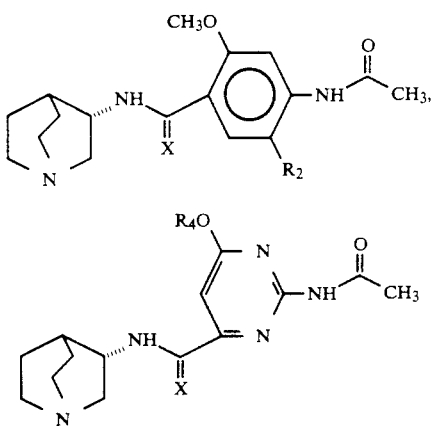

where $R_2$ and $R_4$ have the same meaning as in the formula (Ia), to a deacetylation reaction, preferably by the action of a strong base such as potassium hydroxide.

Laevorotatory 3-aminoquinuclidine of absolute configuration S is also a new compound, since only the racemic mixture of 3-aminoquinuclidine is known from EP-A-0,099,789. It hence falls within the scope of the present invention. It may be prepared by two different routes, namely:

(i) the action of D-tartaric acid on N-(3-quinuclidinyl)-3-chlorobenzamide, resolution by crystallization of the diastereo isomeric salts thereby formed to obtain laevorotatory N-(3-quinuclidinyl)-3-chlorobenzamide D-tartrate, and the action of a base such as an alkali metal hydroxide on this tartrate to obtain (S)-(−)-N-(3-quinuclidinyl)-3-chlorobenzamide, followed by the acid hydrolysis of this S-(−) amide, or (ii) the reaction of quinuclidinone with (R)-α-methylbenzylamine to obtain (R)-N-(α-methylbenzyl)-3-quinuclidinimine and reduction of this imine with an alkali metal borohydride to obtain (S)-N-[(R)-α-methylbenzyl]-3-aminoquinuclidine, followed by hydrogenolysis of the latter in acid medium. It will be noted that dextrorotatory 3-aminoquinuclidine of absolute configuration R may be obtained by route (i) above, but using L-tartaric acid in place of D-tartaric acid, or by route (ii) above, but using (S)-α-methylbenzylamine in place of (R)-α-methylbenzylamine.

The preparations below are given by way of example in order to illustrate the invention.

EXAMPLE 1

Preparation of (S)-(-)-3-aminoquinuclidine

A/ First synthetic route (resolution of the diastereoisomeric salts):

1st stage: Preparation of (S)-(-)-N-(3-quinuclidinyl)-3-chlorobenzamide

N-(3-Quinuclidinyl)-3-chlorobenzamide (52.5 g) dissolved in methanol is added to a solution of D-tartaric acid (29.7 g) in methanol. The precipitate obtained is collected by filtration and treated twice with methanol under reflux. The salt thus purified (20 g) is decomposed with aqueous sodium hydroxide solution and the product extracted with chloroform. After the organic phase has been dried and evaporated, the base obtained is treated in acetone with ethanolic hydrogen chloride solution. The hydrochloride which precipitates is collected by filtration and recrystallized in ethanol. 9.4 g of optically pure (S)-(−)-N-(3-quinuclidinyl)-3-chlorobenzamide hydrochloride are obtained.

Melting point: 244–247° C.

$[\alpha]^{20}_D = 3116.8°$ (c=1, $CH_3OH$)

2nd stage: Preparation of (S)-(−)-3-aminoquinuclidine dihydrochloride

The hydrochloride obtained in the preceding stage (9 g) is treated under reflux for 3 hours 30 minutes with concentrated hydrochloric acid. The reaction medium is cooled, filtered and concentrated to dryness. The residue is treated with absolute ethanol and the (S)-(−)-3-aminoquinuclidine dihydrochloride which crystallizes is collected by filtration.

Melting point: >260° C.

$[\alpha]^{20}_D = -24.9°$ (c=1, $H_2O$).

The R antipode is obtained under the same conditions, using L-tartaric acid as resolving agent.

Melting point >260° C.

$[\alpha]^{20}_D = +24.8°$ (c=1, $H_2O$).

B/ Asymmetric synthesis

1st stage: Preparation of (R)-N-(o-methylbenzyl)-3-quinuclidinimine

Quinuclidinone (80 g) in 800 ml of toluene is brought to reflux in the presence of (R)-α-methylbenzylamine (77.4 g) for 24 h, the water formed being removed with a Dean Stark apparatus. The reaction medium is then concentrated to dryness and the imine formed (130 g) is distilled.

Yield: 89%

Boiling point: 140–150° C. (0.05 mm Hg)

$[\alpha]^{20}_D + 97.2°$ (c=1, $CHCL_3$).

2nd stage: Preparation of (S)-N-[(R)-α-methylbenzyl]-3-aminoquinuclidine dihydrochloride The imine (129.5 g) obtained in the preceding stage is dissolved in methanol and potassium borohydride (30.6 g) is added in small portions at between 10 and 20° C. After one hour, the medium is evaporated to dryness under reduced pressure. The residue is dissolved in a mixture of acetone and isopropyl alcohol (2:1). The expected amine is precipitated in the form of the dihydrochloride by adding ethanolic hydrogen chloride solution. The product is recrystallized twice in an ethanol/methanol (1 1) mixture to obtain optically pure (S)-N-[(R)-α-methylbenzyl]-3-aminoquinuclidine dihydrochloride (81 g).

Yield: 47%

Melting point: >260° C.

$[\alpha]^{20}_D = -2°$ (c=2, $H_2O$). 3rd stage: Preparation of (S)-(−)-3-aminoquinuclidine dihydrochloride The product obtained in the preceding stage (64.4 g) is dissolved in ethanol with 2 equivalents of 1N hydrochloric acid solution and palladium on charcoal, 50% $H_2O$ (12.8 g). The reaction medium is stirred for 18 h under a hydrogen atmosphere, filtered, and then evaporated to dryness under reduced pressure. (S)-(−)-3-aminoquinuclidine dihydrochloride is crystallized in an ethanol/ether (1:1) mixture.

$[\alpha]^{20}_D = -24.2°$ (c=1, $H_2O$).

The R-(+) antipode is obtained by the same sequence of reactions, starting with (S)-α-methylbenzylamine.

EXAMPLE 2

Stereospecific synthesis of N-(3-quinuclidinyl)-4-amino-5-chloro-2-meth oride, S-(−) isomer [code MD 200054] and R-(+) isomer [code MD 200051]

1st variant (S)-(−)-3-Aminoquinuclidine dihydrochloride (40 g; 0.2 mole) is dissolved in 80 ml of 2.5 N aqueous sodium hydroxide solution. 4-Amino-5-chloro-2-methoxybenzoic acid (44.5 g) dissolved in 300 ml of pyridine is added to this solution, cooled in an ice bath. Dicyclohexylcarbodiimide (85 g) is added in two portions. The mixture is stirred vigorously for 18 h at room temperature. The medium is then diluted with 150 ml of water. The insoluble material is removed by filtration and washed with water. The aqueous phase is brought to pH 10 with 10 N sodium hydroxide solution and extracted with chloroform. After the organic phase has been dried (over $Na_2SO_4$) and evaporated, the residue is crystallized in isopropyl ether.

The solid obtained (56 g) is dissolved in 280 ml of isopropyl alcohol and the solution acidified with 5N HCl. The hydrochloride which precipitates is collected by filtration and recrystallized in 99% pure ethanol. The desired product (MD 200054) is obtained in a 60% yield.

Melting point: 233–235° C.

$[\alpha]^{25}_D = -3.9°$ (c=1, $H_2O$).

The dextrorotatory antipode (MD 200051) is obtained under the same conditions, starting with (R)-(+)-3-aminoquinuclidine dihydrochloride.

Melting point: 232–234° C.

$[\alpha]^{20}_D = +3.8°$ (c=1, $H_2O$).

2nd variant:

(S)-(−)-3-Aminoquinuclidine (1.9 g) is dissolved in 33.5 ml of 1N aqueous sodium hydroxide solution. 4-Acetamido-5-chloro-2-methoxybenzoyl chloride (3.75 g) dissolved in 70 ml of dioxane is added dropwise to this solution. After 15 minutes' stirring, the medium is acidified, washed with chloroform and alkalinized with concentrated aqueous sodium hydroxide solution, and the product extracted with chloroform. The organic phase is dried (over $Na_2SO_4$) and then evaporated. The oily residue is dissolved in ethanol and ethanolic hydrogen chloride is added until an acid pH is obtained. The N-(3-quinuclidinyl)-4-acetamido-5-chloro-2-methoxybenzamide hydrochloride thereby formed precipitates (quantitative yield), and the latter is collected by filtration.

The product is then deacetylated by treating it under reflux for 30 minutes in a 5% strength solution of potassium hydroxide in ethanol.

The reaction medium is then dissolved in water and extracted with chloroform. After the organic phase has been dried and evaporated, the hydrochloride MD 200054 is prepared and isolated as above.

$[\alpha]^{20}_D = -3.7°$ (c=1, $H_2O$).

The other enantiomers according to the invention are obtained by procedures similar to those of Example 2, but using appropriate starting reactants.

The compounds according to the invention were studied in laboratory animals and were shown to have activity with respect to the digestive system and, in particular, activity with respect to gastric movements and antiemetic activity.

By way of example, the antiemetic activity of N-(3-quinuclidinyl)-4-amino-5-chloro-2-methoxybenzamide hydrochloride, administered orally in the form of the racemic mixture (code MD 780209), of the laevorotatory enantiomer of configuration S (code MD 200054) and of the dextrorotatory enantiomer of configuration R (code MD 200051), was studied in relation to cisplatin-induced vomiting in dogs.

1/ Method

The method is derived from that described by J. A. GYLYS et al (Res. Commun. Chem. Pathol. Pharmacol. 1979, 23, no. 1, p.61–68). Vomiting is induced by the intravenous injection of cisplatin (INN) at a dose of 3 mg/kg in a random sample of male and female dogs weighing between 10 and 16 kg, which have been maintained on a fluid diet (hydric diet) for 24 hours.

The test compounds are administered orally 60 minutes after the injection of cisplatin.

The animals are fed 1 h 30 min after the treatment. The observation period is 6 hours following the injection of cisplatin.

2/ Results (4 dogs per treatment)

| TREATMENT | DOSE μg/kg | AVERAGE NUMBER | % DECREASE IN NUMBER | % DECREASE AS ALL OR NONE |
|---|---|---|---|---|
| CONTROL (distilled water) | 0 | 10.8 | | |
| MD 780209 (racemic) | 15 | 2 | 81.4 | 25 |
| MD 200054 (−) | 7.5 | 0.5 | 95.3 | 75 |
| MD 200051 (+) | 30 | 7 | 34.9 | 0 |

The results collated in the table above clearly demonstrate that the laevorotatory enantiomer of configuration (code MD 200054) is, surprisingly, much more active in inhibiting vomiting induced by anticancer drugs such as cisplatin than its antipode (code MD 200051) and the corresponding racemate. Furthermore, the laevorotatory enantiomer exhibits fewer side effects than the dextrorotatory enantiomer.

The compounds according to the invention do not exhibit significant toxicity at the active doses shown in the table above; they find their application as medicinal products in the field of the digestive system, in particular as antiemetic agents.

The present invention finally encompasses the pharmaceutical compositions containing, by way of active principal, at least one compound chosen from the enantiomers of absolute configuration S of the derivatives of formula (I), their addition salts with a pharmaceutically acceptable organic or inorganic acid and the hydrates of these enantiomers and salts, in combination with a suitable vehicle. These compositions may be administered orally in the form of gelatin capsules, tablets, dragees and the like, at dosages which can reach 500 mg of active principal per day (in one or more doses), or parenterally in the form of injectable solutions, at dosages which can reach 200 mg of active principal per day (in one or more daily doses).

We claim:
1. Process for preparing laevorotatory 3-aminoquinuclidine of absolute configuration S, consisting of:
   (i) reacting quinuclidinone with (R)-α-methylbenzylamine to obtain (R)-N-(α-methylbenzyl)-3-quinuclidinimine,
   (ii) reducing this imine with an alkali metal borohydride to obtain (S)-N-[(R)-α-methylbenzyl]-3-aminoquinuclidine, and then
   (iii) subjecting the latter to a hydrogenolysis in acid medium.

2. Process for preparing dextrorotory 3-aminoquinuclidine of absolute configuration R, comprising the steps of:
   (i) reacting quinuclidinone with (S)-α-methylbenzylamine to obtain (S)-N-(α-methylbenzyl)-3-quinuclidinimine,
   (ii) reducing this imine with an alkali metal borohydride to obtain (R)-N-[(S)-α-methylbenzyl]-3-aminoquinuclidine, and then
   (iii) subjecting the latter to a hydrogenolysis in acid medium.

* * * * *